United States Patent [19]

Proctor

[11] Patent Number: 5,894,079
[45] Date of Patent: Apr. 13, 1999

[54] FIELD BEAN CULTIVAR NAMED ENOLA

[76] Inventor: Larry M. Proctor, 269 State Hwy. 348, Delta, Colo. 81416

[21] Appl. No.: 08/749,449

[22] Filed: Nov. 15, 1996

[51] Int. Cl.⁶ .............................. A01H 5/00; A01H 1/04
[52] U.S. Cl. ...................... 800/200; 800/205; 800/255; 800/DIG. 23; 47/58
[58] Field of Search ....................... 800/200, 205, 800/250, 255, DIG. 23; 47/57.6, 58

[56] References Cited

U.S. PATENT DOCUMENTS

| | | | |
|---|---|---|---|
| 4,378,655 | 4/1983 | Johnson | 47/58 |
| 4,769,512 | 9/1988 | Schulbach | 800/1 |
| 5,215,912 | 6/1993 | Hoffman | 435/240.4 |
| 5,270,200 | 12/1993 | Sun et al. | 435/240.2 |
| 5,376,543 | 12/1994 | Chee et al. | 435/172.3 |
| 5,530,183 | 6/1996 | Fehr et al. | 800/200 |
| 5,543,576 | 8/1996 | van Ooigen et al. | 800/250 |
| 5,557,036 | 9/1996 | Doane et al. | 800/200 |
| 5,576,203 | 11/1996 | Hoffman | 435/172.3 |
| 5,576,476 | 11/1996 | Moots | 800/200 |
| 5,589,623 | 12/1996 | Ferro et al. | 800/205 |

OTHER PUBLICATIONS

Paredes–Lopez et al. Effect of the hardening phenomenom on some physico–chemical properties of common bean. Food Chemistry, 31:225–236, 1989.

Souza et al. Sample size for estimating the within plot variance in experiments designed to evaluate common bean progenies. Revista Brasileira Genetica, 16:977–982, 1993.

Primary Examiner—Douglas W. Robinson
Assistant Examiner—Melissa L. Kimball
Attorney, Agent, or Firm—Rockey, Milnamow & Katz, Ltd.

[57] ABSTRACT

This invention relates to a new field bean variety that produces distinctly colored yellow seed which remain relatively unchanged by season. The invention also relates to a method for producing a field bean plant by crossing a first parent field bean plant with a second parent field bean plant, wherein the first and/or second field bean plant is the field bean plant of the present invention.

15 Claims, 3 Drawing Sheets

FIELD BEAN CULTIVAR NAMED ENOLA

FIELD OF THE INVENTION

This invention relates to a new field bean variety that produces distinctly yellow colored seed which remain relatively unchanged by season.

BACKGROUND OF THE INVENTION

Dry edible field beans (*Phaseolus vulgaris*) such as pintos, great northerns, navies, kidneys, blacks, pinks, etc., contain no cholesterol and very little fat. In combination with other foods, they serve as a complete source of protein. In fact, one cup of cooked dry field beans contains approximately 35% of the U.S. recommended daily allowance of protein.

Beans are also an important source of natural (dietary) fiber, which is a necessary part of the human diet. Dietary fiber is the undigestible part of the foods we eat. Beans possess more dietary fiber per serving than any other unprocessed food. For example, one-half cup of cooked beans contributes up to 6.78 grams of dietary fiber. Other foods high in dietary fiber include other legumes, bran, whole grain breads and cereals, fruits and vegetables.

There are two types of dietary fiber, insoluble and soluble. Insoluble fiber acts in the intestine to increase bulk and relieve constipation. Soluble fiber helps lower blood sugar and cholesterol levels. This means better control for people with diabetes or high blood cholesterol. One study found that by including beans in the daily diet, that blood cholesterol levels were reduced by 10 to 20%. Colorado Dry Bean Advisory Board, *Bean Recipes and Nutrition Facts*, Colorado Department of Agriculture (1988).

Beans are also a rich source of vitamins and minerals, including iron, potassium, calcium, zinc, magnesium, phosphorus and other trace minerals. They are also a rich natural source of B-complex vitamins.

As demonstrated above, field beans are an important and valuable field crop. Thus, a continuing goal of plant breeders is to discover and develop stable, high yielding bean cultivars that are agronomically sound. To accomplish this goal, the bean breeder must discover, select and develop bean plants that have the traits that result in superior cultivars.

SUMMARY OF THE INVENTION

The present invention involves a field bean cultivar named "Enola". The field bean cultivar Enola produces a distinct and completely yellow colored seed. The yellow color of the seed remains uniform and stable from season to season. The present invention also relates to a method for producing a field bean plant by crossing a first parent field bean plant with a second parent field bean plant, wherein the first and/or second field bean plant is the field bean plant of the present invention.

BRIEF DESCRIPTION OF THE DRAWINGS

The file of this patent contains at least one color photograph. Copies of this patent with the color photographs will be provided by the Patent and Trademark Office upon request and payment of the necessary fee.

DEFINITIONS

Figure 1:
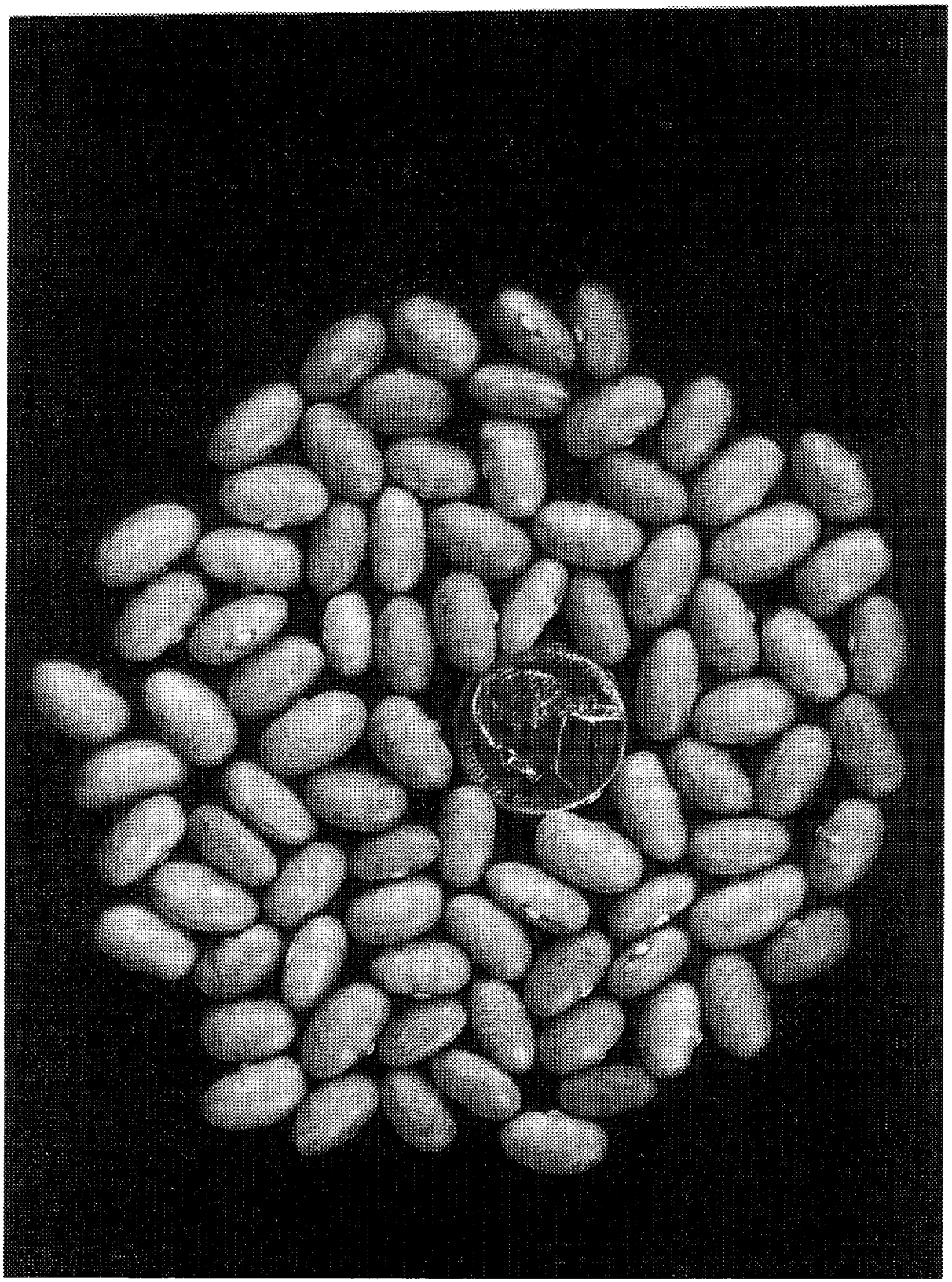
FIG. 1 shows a color photograph of several yellow colored bean seeds of the field bean cultivar Enola.

In the description and tables which follow, a number of terms are used. In order to provide a clear and consistent understanding of the specification and claims, including the scope to be given such terms, the following definitions are provided:

Maturity. Plants are considered mature when 95% of the pods have received their mature color.

Plant Height. Plant height is taken from the top of soil to the top of the plant and is measured in centimeters.

*Munsell Book of Color*. *Munsell Book of Color* refers to the *Munsell Book of Color*, Neighboring Hues Edition, Matte Finish Collection, 1973 (Call Number ND 1285.M83 1973), herein incorporated by reference. The *Munsell Book of Color* contains the system of color notation developed by A. H. Munsell that identifies color in terms of three attributes: hue, value and chroma. The three attributes of color are arranged into orderly scales of equal visual steps; the scales are used as dimensions or parameters for the accurate specification and description of color under standard conditions of illumination and viewing in natural lighting.

The hue (H) notation of a color indicates its relation to a visually equally-spaced scale of 100 hues. There are ten major hues (five principal and five intermediate) positioned ten hue steps apart within this scale. The hue notation in general use is based on the ten major hue names, Red, Yellow-Red, Yellow, Green-yellow, Green, Blue-Green, Blue, Purple-Blue, Purple and Red-Purple.

The value (V) notation indicates the lightness or darkness of a color in relation to a neutral gray scale, which extends from absolute black to absolute white. The value symbol 0 is used for absolute black, the symbol 10 is used for absolute white. The symbol 5 is used for the middle gray and for all chromatic colors that appear half way in value between absolute black and absolute white.

The chroma (C) notation indicates the degree of departure of a given hue from a neutral gray of the same value. The scales of chroma extend from 0 for a neutral gray out to 10, 12, 14 or farther, depending upon the strength (saturation) of the sample to e evaluated.

The complete Munsell notation for a chromatic color is written H V/C. For example, seed having the Munsell color 7.5 Y 8.5/6. The 7.5 Y represents the hue, 8.5 represents the value, and 6 is the chroma.

DETAILED DESCRIPTION OF THE INVENTION

The present invention relates to a field bean (*Phaseolus vulgaris*) cultivar that produces seed having a distinctive yellow color. The yellow color is present throughout the entire seed coat and remains uniform and stable season after season, when viewed in natural lighting.

In 1994, field beans that were yellow in color were discovered in a package of dry edible beans purchased in Mexico and brought to the United States. This package of beans contained a variety of different types of beans including browns, blacks, pintos, etc. Later in 1994, the yellow field beans selected from the package of miscellaneous beans were planted in Montrose County, Colorado and allowed to self-pollinate. A segregating population of plants resulted. Many of the resulting plants exhibited abnormally large leaves, approximately twice the size of the leaves of the cultivar of the present invention, and produced pods containing yellow seeds. Additionally, a large number of the plants also produced pods that did not adhere well to the branches of the plant and fell to the ground and other pods exhibited shattering prior to harvest. Individual plants exhibiting small leaves, good adherence of the pod to the branches of the plant, as well as resistance to pod shattering, were selected and harvested individually.

The harvested seeds were planted in 1995 in Montrose County, Colorado and allowed to self-pollinate. Most of the resulting plants exhibited uniform leaf size. Individual plants exhibiting good adherence of the pod to the branches of the plant, resistance to pod shattering and yields greater than the average yield of an average commercial bean plant (the average commercial pinto bean plant yields approximately 3.1 pinto beans per pod) were selected and harvested individually.

These harvested seeds were planted in 1996 in Montrose County, Colorado and allowed to self-pollinate. The resulting plants exhibited uniform leaf size. Individual plants exhibiting the good adherence of the pod to the plant, higher yield, and resistance to pod shattering were selected and harvested and bulked to produce the cultivar of the present invention.

Figure 2:
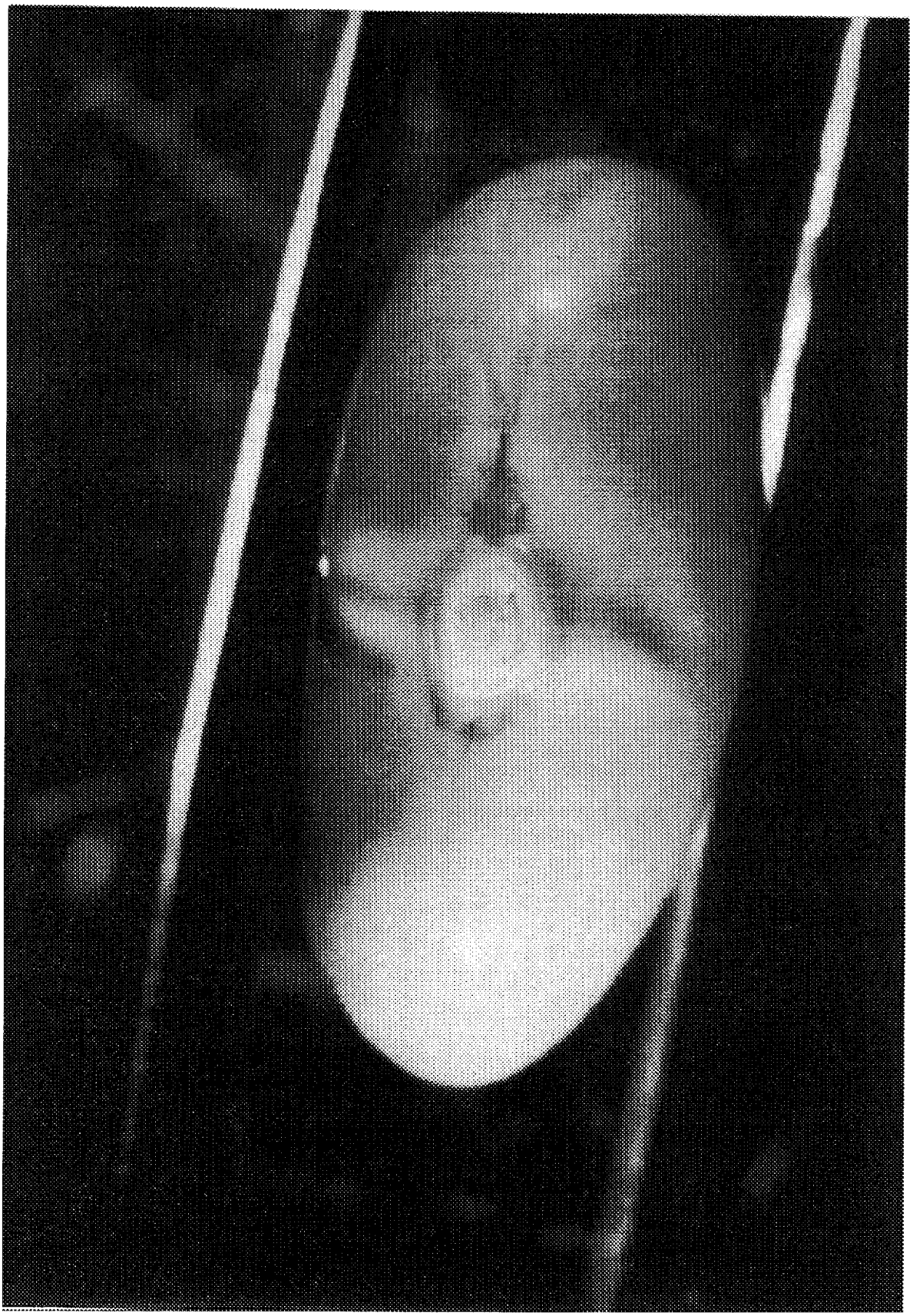
FIG. 2 shows a color photograph of a close-up of the seed of the variety Enola. The seed of Enola has a yellow color (matching most closely 7.5 Y 8.5/4 to 7.5 Y 8.5/6 in the *Munsell Book of Color* when viewed in natural light) throughout its seed coat and a tan/yellow (matching most closely 2.5 Y 9/4 to 2.5 Y 9/6 in the *Munsell Book of Color* when viewed in natural light) hilar ring.

The field bean cultivar Enola exhibits superior characteristics over other classes of field bean cultivars. More specifically, Enola seed possesses a unique yellow color, matching most closely to 7.5 Y 8.5/4 to 7.5 Y 8.5/6 in the *Munsell Book of Color*, when viewed in natural light. Unlike the seed produced by the "Yellow Eye" class of dry field beans, such as the cultivar Steuben, in which the yellow color is restricted only to the "eye" of the seed, the yellow color of the Enola seed is present throughout the entire seed coat. The hilar ring of Enola is tan/yellow in color, matching most closely 2.5 Y 9/4 to 2.5 Y 9/6 in the *Munsell Book of Color*, when viewed in natural light. FIG. 1 is a color photograph of the yellow bean seeds of Enola. This photograph demonstrates that the entire seed coat of the bean is yellow in color. FIG. 2 is a close-up color photograph of the yellow seed of Enola. This photograph demonstrates that the entire seed coat of Enola seed, including the hilar ring, is yellow in color. The yellow color of the Enola seed remains relatively unchanged by season. "Relatively unchanged by season" means that the color of the seed remains uniform and stable from season to season.

Figure 3:
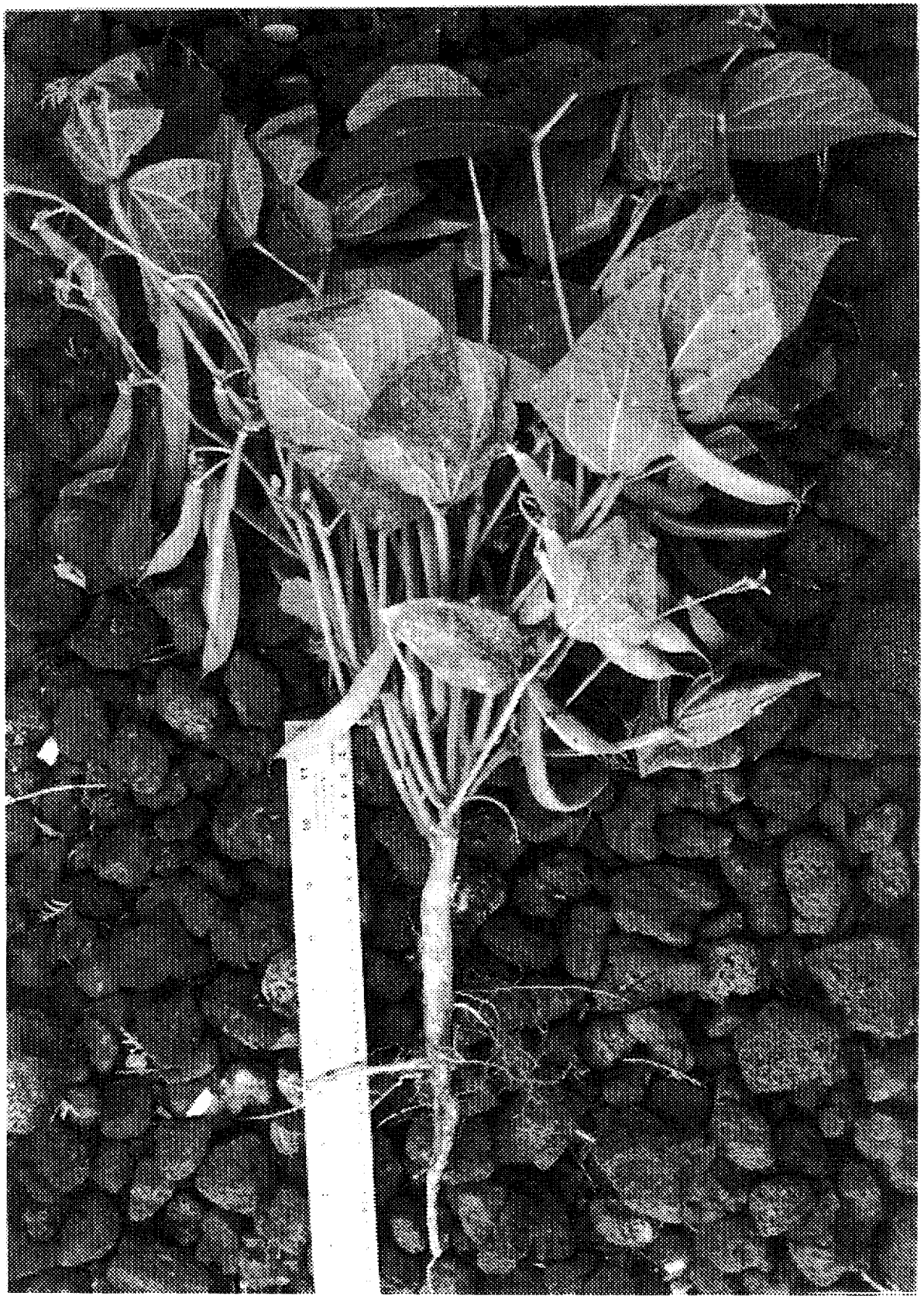
FIG. 3 shows a color photograph of the dry field bean cultivar Enola, including its stem, branches, leaves, pods and root structure.

FIG. 3 shows a color photograph of the field bean cultivar Enola. The photograph shows the wood-like stalk of the cultivar and its wrinkled and dull ovate shaped leaves. The photograph also demonstrates the long, branching root structure of the plant, which is unusual for a field bean cultivar. The root structure of most field bean cultivars (such as pintos) would be described as follows. Beginning at, or just below the soil line, the root averages 0.5 cm±in caliper size and branches into a mass of roots consisting of a main taproot, leader or stabilizing roots, and feeder roots, all of soft plant tissue extending up into the stem and branches of the plant. The main taproot is generally of the same size or slightly larger than the leader and feeder roots. Since the root system is not heavy in mass and does not extend very deep into the soil, these beans are "pulled" at harvest time. The yellow "Enola" variety establishes a long deep-growing taproot averaging 1.0 cm±in caliper size, a leader root of slightly lesser size, and even smaller feeder roots, all of the same wood-like tissue that extends upward into the stem. Due to the size and wood-like tissue structure, the Enola bean must be cut or "knifed" at harvest time.

The pods produced by the cultivar Enola adhere strongly to the branches of the plant. There is minimal dropping of the pods from the branches, under normal or adverse climatic conditions which is a significant problem in other field bean varieties. Additionally, the pods of Enola exhibit good tightness, which is helpful in keeping out moisture, which lessens seed damage, thereby improving the quality of the seed. Seed damage due to moisture has been a problem in other field bean varieties. Typically, once moisture gets into the pods of a bean plant, the pods swell, then shrink, and then eventually open, releasing their seeds into the growing area. Finally, the pods of Enola exhibit very little shattering prior to harvest.

The distinctly yellow colored bean seeds of Enola are edible for human consumption. Unlike other dry field beans which have a gritty type of texture and taste, the bean seeds of Enola have a smooth texture and taste. Additionally, the bean seeds of Enola have the ability to take on a large volume of water when soaked prior to cooking. Furthermore, the bean seeds of Enola have been found to cook up faster, in approximately one-half the time, of other dry field beans. For example, two pots containing the yellow bean seeds of the present invention can be cooked in the same amount of time that it takes to cook just one pot of pinto bean seeds.

The cultivar has shown uniformity and stability for all traits, as described in the Example 1, which contains a description of variety information. The cultivar has been self-pollinated a sufficient number of generations, with careful attention to uniformity of plant type to ensure phenotypic stability. The cultivar has been increased with continued observation for uniformity. No variant traits have been observed or are expected in Enola.

This invention is also directed to methods for producing a field bean plant by crossing a first parent field bean plant with a second parent field bean plant, wherein the first or second field bean plant is the field bean plant Enola. Further, both first and second parent field bean plants may be from the cultivar Enola. Therefore, any method using the cultivar Enola is part of this invention: selfing, backcrosses, hybrid breeding, and crosses to populations.

As used herein, the term "plant" includes plant cells, plant protoplasts, plant cells of tissue culture from which field bean plants can be regenerated, plant calli, plant clumps, and plant cells that are intact in plants or parts of plants, such as pollen, flowers, seeds, pods, leaves, stems, and the like. Thus, another aspect of this invention is to provide for cells which upon growth and differentiation produce the cultivar Enola.

By way of example, not of limitation, the following examples are given.

EXAMPLE 1

Morphological Description of Enola

The field bean cultivar Enola will not be described. The terminology used herein to describe Enola are those used by the Plant Variety Protection Office, unless otherwise noted, in Exhibit C, "Objective Description of the Variety Edible Bean (*Phaseolus vulgaris* L.).

1. PLANT VARIETY. Enola is a dry field bean variety. Genus and Species Name: *Phaseolis vulgaris*. Family name: Leguminosae.

2. PLANT HABIT. Enola is in the form of bush—determinate, with a strong and erect stem and branches. The average height of the mature plant is 34.9 cm. The position of the pod on the plant is scattered. The variety exhibits good lodging resistance through maturity, and does not fall over easily when subjected to wind and other climatic conditions. The variety is not adapted for machine harvesting.

3. LEAF MORPHOLOGY. The mature leaves are wrinkled and dull and the overall shape of the leaves is ovate. The apex of the leaves are acuminate and the base is obtuse.

4. FLOWER COLOR. The color of the flowers, wings and keel is white.

5. POD MORPHOLOGY.

ONSET—At onset, the color of the pod is green (matching most closely 5 GY 6/6 in the *Munsell Book of Color* when viewed in natural light) and the color pattern of the pod is solid. The pod exhibits a pear shape cross section. The curvature of the pod is straight and the orientation of the pod beak is also straight. The pod exhibits slight constrictions.

MATURITY—At maturity, the color of the pod is tan (matching most closely 5 Y 8.5/6 in the *Munsell Book of Color* when viewed in natural light) and the color pattern of the pod is solid. The pod exhibits a pear shape cross section. The curvature of the pod is slightly curved and the orientation of the pod break is variable. The average break length of the pod is 1.2 cm. The pod also exhibits slight constrictions. The number of seeds per pod is approximately 3.1.

6. SEED COLOR. The seeds are shiny and monochrome. The primary color of the seeds is yellow (matching most closely 7.5 Y 8.5/4 to 7.5 Y 8.5/6 in the *Munsell Book of Color* when viewed in natural light). The seeds do not have a secondary color. The color of the hilar ring is tan/yellow (matching most closely 2.5 Y 9/4 to 2.5 Y 9/6 in the *Munsell Book of Color* when viewed in natural light). Light is not required for the germination of the seeds.

7. SEED SHAPE AND WEIGHT. The shape of the seed taken from the middle of the pod is cuboid. The dry seed weight of 43 grams per 100 seeds (adjusted to 12 percent moisture).

8. ANTHOCYANIN PIGMENTATION. Anthocyanin pigmentation is absent in the flowers, stems, pods, seeds, leaves, petioles, peduncles and nodes.

9. DISEASE AND STRESS REACTIONS. Enola is tolerant to heat. Enola exhibits some resistance to Fusarium root rot.

10. MISCELLANEOUS INFORMATION. The estimated maturity is late (101 days).

EXAMPLE 2

Propagation of Enola

Production of market ready beans from Enola proceeds as follows. Seed is directly sown one at a time in rows in a bed. The rows on a bed are about 30 inches apart with seed deposited at intervals of approximately 1½ to 1¾ inches along the row.

In Montrose County, Colorado, the plants are watered during the germination phase using a gravity flow system. As the plants grow, they require water approximately every 7 to 10 days.

In mineral soils common in the west, fertilization with nitrogen, phosphorus and, less frequently, potassium is required.

Harvest time various according to the local climatic conditions. Enola takes approximately 100 to 105 days from planting to harvest in Colorado.

At maturity, the plants are knifed and put into a windrow and allowed to dry. Drying takes approximately 5 to 8 days. Once dried, the plants are combined using a conventional combine.

Deposit of Enola

Seeds of Enola have been deposited with the American Type Culture Collection, 12301 Parklawn Drive, Rockville, Md. 20852. The deposit was made on Dec. 11, 1997 and received accession number ATCC 209549. This deposit was made in compliance with the Budapest Treat requirements that the duration of the deposit should be for thirty (30) years from the date of deposit or for five (5) years after the last request for the deposit at the depository or for the enforceable life of a U.S. Patent that matures from this application, whichever is longer. Seeds of Enola will be replenished should it become non-viable at the depository.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A *Phaseolus vulgaris* field bean seed designated Enola as deposited with the American Type Culture Collection under accession number 209549.

2. A field bean plant produced by growing the seed of claim 1.

3. Pollen of the plant of claim 2.

4. A field bean plant having all the physiological and morphological characteristics of the field bean plant of claim 2.

5. A method of producing a field bean plant comprising crossing a first parent field bean plant with a second parent field bean plant, wherein the first field bean plant is the field bean plant of claim 2.

6. A method of producing a field bean plant comprising crossing a first parent field bean plant with a second parent field bean plant, wherein the second field bean plant is the field bean plant of claim 2.

7. A method of producing a field bean plant comprising crossing a first parent field bean plant with a second parent field bean plant, wherein the first and second field bean plant is the field bean plant of claim 2.

8. A field bean variety of *Phaseolus vulgaris* that produces seed having a seed coat that is yellow in color, wherein the yellow color is from about 7.5 Y 8.5/4 to about 7.5 Y 8.5/6 in the *Munsell Book of Color* when viewed in natural light.

9. The *Phaseolus vulgaris* of claim 8 wherein the seed further comprises a hilar ring.

10. The *Phaseolus vulgaris* of claim 9 wherein the hilar ring has a color of rom about 2.5 Y 9/4 to about 2.5 Y 9/6 in the *Munsell Book of Color* when viewed in natural light.

11. Propagation material of the *Phaseolus vulgaris* of claim 8.

12. Pollen of the *Phaseolus vulgaris* of claim 8.

13. Seed from a field bean variety of *Phaseolus vulgaris* that is completely yellow in color, wherein the yellow color is from about 7.5 Y 8.5/4 to about 7.5 Y 8.5/6 in the *Munsell Book of Color*.

14. Seed of claim 13 further comprising a hilar ring.

15. Seed of claim 14 wherein the color of the hilar ring is from about 2.5 Y 9/4 to about 2.5 Y 9/6 in the *Munsell Book of Color* when viewed in natural light.

* * * * *

UNITED STATES PATENT AND TRADEMARK OFFICE
CERTIFICATE OF CORRECTION

PATENT NO. : 5,894,079
DATED : April 13, 1999
INVENTOR(S) : Larry M. Proctor

It is certified that error appears in the above-indentified patent and that said Letters Patent is hereby corrected as shown below:

```
Column 2, line 49, delete "e" and insert --be--.
Column 6, line 55, delete "rom" and insert --from--.
```

Signed and Sealed this

Twenty-second Day of May, 2001

Attest:

NICHOLAS P. GODICI

*Attesting Officer*     *Acting Director of the United States Patent and Trademark Office*

US005894079C1

(12) EX PARTE REEXAMINATION CERTIFICATE (8002nd)
United States Patent
Proctor

(10) Number: US 5,894,079 C1
(45) Certificate Issued: Jan. 25, 2011

(54) FIELD BEAN CULTIVAR NAMED ENOLA

(75) Inventor: Larry M. Proctor, Delta, CO (US)

(73) Assignee: Pod-Ners, L.L.C., Delta, CO (US)

Reexamination Request:
No. 90/005,892, Dec. 20, 2000

Reexamination Certificate for:
Patent No.: 5,894,079
Issued: Apr. 13, 1999
Appl. No.: 08/749,449
Filed: Nov. 15, 1996

Certificate of Correction issued May 22, 2001.

(51) Int. Cl.
*A01H 5/10* (2006.01)

(52) U.S. Cl. ..................................... 800/260; 800/313
(58) Field of Classification Search .................. 800/313
See application file for complete search history.

(56) References Cited

PUBLICATIONS

Pallottini et al. Crop Sci. 44: 968–977, 2004.*
hyperphysics.phy–astr.gsu.edu/hbase/vision/specol.html, Mar. 30, 2005.*
usna.usda.gov/Gardens/glossary.html, Apr. 1, 2005.*
victoryseeds.com/information/glossary.html, Apr. 1, 2005.*
GRIN Accession No. PI 312090 (1966).*
GRIN Accession No. PI 208777 (1953).*
GRIN Accession No. PI 282060 (1962).*
Coulibaly S., et al.; AFLP Analysis of the phenetic organization and genetic diversity of *Vigna unguiculate* L. Walp. reveals extension gene flow between wild and domesticated types; Theor. Appl. Genet., vol. 104 (2002), pp. 358–366.
Quedraogo J.T. et al.; An Improved genetic linkage map for cowpea (*Vigna unguiculata* L.) Combining AFLP, RFLP and RAPD, biochemical markers, and biological resistance traits; Genome, vol. 45 (2002), pp. 175–188, Canada.
Miklas, P. N., et al.; QTL Conditioning Physiological Resistance and Avoidance to White Mold in Dry Bean; Crop Science, Mar.–Apr. 2001, vol. 41, pp. 309–315.
Yu K., et al.; Integration of Simple Sequence Repeat (SSR) Markers Into a Molecular Linkage Map of Common Bean (*Phaseolus vulgaris* L.); The American Genetic Association, vol. 91 (2000), pp. 429–434.
Pasquet, R.S., et al.; Isozyme Diversity in Bambara Groundnut.; Crop Science, Jul.–Aug. 1999, vol. 39 pp. 1228–1236.
Johnson, W.C., et al.; Segregation for performance in recombinant inbred populations resulting from inter–gene pool crosses of common bean (*Phaseolus vulgaris* L.); Euphytica, vol. 106 (1999), pp. 45–56, Netherlands.
Tsai, S.M., et al.; QTL mapping for nodule number and common bacterial blight in *Phaseolus vulgaris* L.; Plant and Soil, vol. 204 (1998), pp. 135–145, Netherlands.
Freyre, R., et al.; Towards an integrated linkage map of common bean. 4. Development of a core map and alignment of RFLP maps; Theor Appl Genet, vol. 97 (1998), pp. 847–856.

Geffroy, V., et al.; A. family of LRR sequences at the *Co–2* locus for anthracnose resistance in *Phaseolus vulgaris* and its potential use in marker–assisted selection; Theor Appl Genet; vol. 96 (1998), pp. 494–502.
Menendez, C.M., et al.; A genetic linkage map of cowpea (*Vigna unguiculata*) developed from a cross between two inbred, domesticated lines; Theor Appl Genet, vol. 95 (1997), pp. 1210–1217.
Johnson, W.C., et al.; Association of a seed weight factor with the phaseolin seed storage protein locus across genotypes, environments, and genomes in *Phaseolus–Vigna* spp.: Sax (1923) revisited; http://www.ncgr.org/jag/papers96/paper596/saxp2.html.
The yellow field bean called Mayacoba filed with CIAT under No. G13094; http://www.ars–grin.gov/npgs/acc/acc_queries.html.
The yellow field bean called Mantequilla filed with CIAT under No. G02400; and in the United States Department of Agriculture under Plant Introduction No. PI312090; http://www.ars–grin.gov/npgs/acc/acc_queries.html.
The yellow field bean called II8FR–MO–5–3–M–2–1–M filed with CIAT under No. G22215; http://www.ars–grin.gov/npgs/acc/acc_queries.html.
The yellow field bean called MO–85–86–2598 filed with CIAT under No. G22227; http://www.ars–grin.gov/npgs/acc/acc_queries.html.
The yellow field bean called MO–85–86–2780 filed with CIAT under No. G22230; http://www.ars–grin.gov/npgs/acc/acc_queries.html.
The yellow field bean called Culiacan–11–57R–M–37–M–M filed with CIAT under No. G11891; http://www.ars–grin.gov/npgs/acc/acc_queries.html.
Azufrado, CIAT bean–G91, USDA #PI150941; http://www.ars–grin.gov/npgs/acc/acc_queries.html.
Azufrado, CIAT bean–G817, USDA #PI197689; http://www.ars–grin.gov/npgs/acc/acc_queries.html.
Azufrado, CIAT bean–G862, USDA #PI201940; http://www.ars–grin.gov/npgs/acc/acc_queries.html.
Azufrado, CIAT bean–G863, USDA #PI201941; http://www.ars–grin.gov/npgs/acc/acc_queries.html.
Azufrado, CIAT bean–G1818, USDA #PI309802; http://www.ars–grin.gov/npgs/acc/acc_queries.html.
Azufrado, CIAT bean–G1823, USDA #PI309808; http://www.ars–grin.gov/npgs/acc/acc_queries.html.
Azufrado, CIAT bean–G1824, USDA #PI309810; http://www.ars–grin.gov/npgs/acc/acc_queries.html.
Azufrado, CIAT bean–G1804, USDA #PI309783; http://www.ars–grin.gov/npgs/acc/acc_queries.html.
Azufrado, CIAT bean–G1807, USDA #PI309787; http://www.ars–grin.gov/npgs/acc/acc_queries.html.

(Continued)

*Primary Examiner*—Gary L Kunz

(57) ABSTRACT

This invention relates to a new field bean variety that produces distinctly colored yellow seed which remain relatively unchanged by season. The invention also relates to a method for producing a field bean plant by crossing a first parent field bean plant with a second parent field bean plant, wherein the first and/or second field bean plant is the field bean plant of the present invention.

PUBLICATIONS

Azufrado, CIAT bean–G1808, USDA #PI309788; http://www.ars-grin.gov/npgs/acc/acc_queries.html.
Azufrado, CIAT bean–G1814, USDA #PI309797; http://www.ars-grin.gov/npgs/acc/acc_queries.html.
Azufrado, CIAT bean–G1815, USDA #PI309799; http://www.ars-grin.gov/npgs/acc/acc_queries.html.
Azufrado, CIAT bean–G2250, USDA #PI311895; http://www.ars-grin.gov/npgs/acc/acc_queries.html.
Azufrado, CIAT bean–G2254, USDA #PI311899; http://www.ars-grin.gov/npgs/acc/acc_queries.html.
Azufrado, CIAT bean–G2843, USDA #PI319649; http://www.ars-grin.gov/npgs/acc/acc_queries.html.
Azufrado, CIAT bean–G2868, USDA PI319678; http://www.ars-grin.gov/npgs/acc/acc_queries.html.
Azufrado, CIAT bean–G2877, USDA #PI319687; http://www.ars-grin.gov/npgs/acc/acc_queries.html.
Azufrado, CIAT bean–G3456, http://www.ars-grin.gov/npgs/acc/acc_queries.html.
Azufrado del Yaqui, CIAT bean–G2403, USDA #PI312093; http://www.ars-grin.gov/npgs/acc/acc_queries.html.
Azufrado Boliot, CIAT bean–G2406, USDA #PI312096; http://www.ars-grin.gov/npgs/acc/acc_queries.html.
Azufrado del Rio, CIAT bean–G2251, USDA #PI311896; http://www.ars-grin.gov/npgs/acc/acc_queries.html.
Azufrado de la Sierra, CIAT bean–G2253, USDA #PI311898; http://www.ars-grin.gov/npgs/acc/acc_queries.html.
Azufrado Mayo, CIAT bean–G405, USDA #PI312095; http://www.ars-grin.gov/npgs/acc/acc_queries.html.
*Phaseolus–Vigna* Genetics and Evolution; Gepts Lab—Publications; Updated May 6, 2002; http://agronomy.ucdavis.edu/gepts/ref.html.
Bassett, Mark J. et al.; Classical and Molecular Genetic Studies of the Strong Greenish Yellow Seedcoat Color in 'Wagenaar' and 'Enola' Common Bean; American Society for Horticultural Science Online; http://www.ashs.org/search.asp.
Bassett, Mark J. et al.; Inheritance of Reverse Margo Seedcoat Pattern and Allelism between the Genes *J* for Seedcoat Color and *L* for Partly Colored Seedcoat Pattern in Common Bean; American Society for Horticultural Science Online; http://www.ashs.org/search.asp.
Bassett, Mark J. et al.; A Brief Review of the Genetics of Partly Colored Seed Coats in Common Bean; http://www.css.msu.edu/bic/reviewarticle.html.
Bassett, Lee, Otto & McLean, "Classical and Molecular Genetic Studies of the Strong Greenish Yellow Seedcoat Color in "Wagenaar" and "Enola" Common Bean", Journal of The American Society for Horticultural Sciences, 2002, pp. 50–55, vol. 127, No. 1, USA.
Native Seeds–Search, Seed listing, 1983.
Native Seeds–Search, Seed listing, 1984.
Native Seeds–Search, Seed listing, 1987 (brochure).
Native Seeds–Search, Seed listing, 1988.
Native Seeds–Search, Seed listing, 1989.
Native Seeds–Search, Seed listing, 2002.
Pallottini, L. Kami, J., Barcaccia, G and Gepts. P. the Genetic Identiti of a Patented Yellow Bean. (2004) Crop Sci. Soc. Am.
Annual Report of the Bean Improvement Cooperative, vol. 47, 2004 pp. 155–162.

Declaration of Gil Waibel, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 7, 2002; 45 pages.

Declaration of Kenneth L. Hines, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 7, 2002; 3 pages.

Declaration of Beulah Hines, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 7, 2002; 2 pages.

Declaration of Russell McDougal, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 9, 2002; 4 pages.

Declaration of Gary L. Knight, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 9, 2002; 2 pages.

Declaration of Christopher A. Greco, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 8, 2002; 3 pages.

Declaration of Scott Harmon, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 7, 2002; 3 pages.

Declaration of Ray Geler, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 8, 2002; 3 pages.

Declaration of Andrew S. Webb, filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 8, 2002; 3 pages.

Expert Report of Paul Gepts, Ph.D., filed in *Pod–Ners, LLC* v. *Northern Feed & Bean of Lucerne, Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 5, 2002; 56 pgs.

Expert Report of Kenneth Grafton, Ph. D, filed in *Pod–Ners, LLC* v. *Northern Feed & Bean of Lucerne, Ltd. Liability Co., et al.,* an action for Infringement of Pod–Ners' Plant Variety Protection Act Certificate currently pending in the United States District Court for the District of Colorado (Civil Action No. 01–WY–2310 AJ); Oct. 2, 2002; 67 pgs.

Grafton, K.F., et al., Row Spacing, Plant Population, and Genotype X Row Spacing Interaction Effects on Yield and Yield Components of Dry Bean; Agronomy Journal, vol. 80, Jul.–Aug. 1988; pp. 631–634.

Adams, M.W.; Basis of Yield Component Compensation in Crop Plants With Special Reference to the Field Bean, *Phaseolus vulgaris*[2] ; Crop Science, vol. 7 Sep.–Oct. 1957; pp. 505–510.

Declaration of Gil Waibel, filed in *Pod–Ners, LLC* v. *Northern Feed & Bean of Lucerne, Ltd. Liability Co., et al.,* an action for Infringement of Pod–Ners' Plant Variety Protection Act Certificate currently pending in the United States District Court for the District of Colorado (Civil Action No. 01–WY–2310 AJ); Oct. 22, 2002; 2 pages.

Declaration of James Nienhuis, filed in *Pod–Ners, LLC* v. *Northern Feed & Bean of Lucerne, Ltd. Liability Co., et al.,* an action for Infringement of Pod–Ners' Plant Variety Protection Act Certificate currently pending in the United States District Court for the District of Colorado (Civil Action No. 01–WY–2310 AJ); Oct. 24, 2002; 59 pgs.

Dorschner, Cheryl; Beans; National Gardening for America's Most Devoted Gardeners; Sep./Oct. 1992; p. 35–37.

Gepts, P., et al; Phaseolin–protein Variability in Wild Forms and Landraces of the Common Bean (*Phaseolus vulgaris*); Evidence for Multiple Centers of Domestication; Economic Botany, 40(4), 1988, pp. 451–468; © 1986, by The New York Botanical Garden, Bronx, NY 10458.

Gepts, P. et al.; Dissemination Pathways of Common Bean (*Phaseolus vulgaris,* Fabaceae) Deduced from Paseolin Electrophoretic Variability. I. The Americas; Economic Botany 42(1); 1988, pp. 73–85; © 1988 by The New York Botanical Garden, Bronx, NY 10458.

Singh, Shree P., et al; Genetic Diversity in Cultivated Common Bean: I. Allozymes; Published in Crop Sci. 31:19–23 (1991).

Singh, Shree P., et al; Genetic Diversity in Cultivated Common Bean: II. Marker–Based Analysis of Morphological and Agronomic Traits; Published in Crop Sci. 31:23–29 (1991).

Gepts, Paul; Phaseolin as an Evolutionary Marker; Genetic Resources of Phaseolus Beans; © 1998 by Kluwer Academic Publishers; pp. 214–241.

Gepts, Paul; A Middle American and an Andean Common Bean Gene Pool; Genetic Resources of Phaseolus Beans; © 1998 by Kluwer Academic Publishers; pp. 375–390.

Singh, Shree P., et al.; Races of Common Bean (*Phaseolus vulgaris,* Fabacea)[1]; Economic Botany 45(3) pp. 379–396. 1991; ® 1991, by The New York Botanical Garden, Bronx, NY 10458 USA.

Gepts, Paul L.; Nutritional and Devolutionary Implications of Phaseolin Seed Protein Variability in Common Bean (*Phaseolus vulgaris* L.); A thesis submitted in partial fulfillment of the requirements for the degree of Doctor of Philosophy (Plant Breeding and Plant Genetics) at the University of Wisconsin–Madison 1984.

Exportacion De Variedades De Frijoi Tipo Azufrado A La U.S.A., 1990.

Jarvis, C.D., American Varieties of Beans; Cornell University; Agricultural Experiment Station of The College of Agriculture, Department of Horticulture, Ithaca, N.Y., Published by the University; Nov. 1908; Bulletin 280; pp. 149–255.

Canario; Peru; bean USDA# PI269207; Aug. 9, 1994; http://www.ars–grin.gov/cgi–bin/npgs/html.

Azufrados; Chill; bean USDA# PI282052; Aug. 9, 1994; http://www.ars–grin.gov/cgi–bin/npgs/html.

Canario LM 57; Peru; bean USDA# PI290995; Aug. 9, 1994; http://www.ars–grin.gov/cgi–bin/npgs/html.

Jalo–90; Brazil; bean USDA# PI298109; Aug. 9, 1994; http://www.ars–grin.gov/cgi–bin/npgs/html.

Frijol Azufrado; Mexico; CIAT bean–G18958; USDA #PI309784; Aug. 9, 1994; http://www.ars–grin.gov/cgi–bin/npgs/html.

Frijol Peruana; Mexico; CIAT bean–G1812; USDA# PI309792; Aug. 9, 1994; http://www.ars–grin.gov/cgi–bin/npgs/html.

Frijol Azufrado; Mexico; CIAT bean–G18959; USDA# PI309794; Aug. 9, 1994; http://www.ars–grin.gov/cgi–bin/npgs/html.

Frijol Azufrado; Mexico; CIAT bean–G18962; USDA# PI309809; Aug. 9, 1994; http://www.ars–grin.gov/cgi–bin/npgs/html.

Frijol Azufrado; Mexico; CIAT bean–G18963; USDA# PI309811; Aug. 9, 1994; http://www.ars–grin.gov/cgi–bin/npgs/html.

Azufrado; Mexico; bean USDA# PI313519; Aug. 9, 1994; http://www.ars–grin.gov/cgi–bin/npgs/html.

Canario; Mexico; CIAT bean–G19136; USDA# PI313530; Aug. 9, 1994; http://www.ars–grin.gov/cgi–bin/npgs/html.

Frijol Azufrado; Mexico; CIAT bean–G19169; USDA# PI325675; Aug. 9, 1994; http://www.ars–grin.gov/cgi–bin/npgs/html.

Canario; Mexico; bean USDA# PI417816; Aug. 9, 1994; http://www.ars–grin.gov/cgi–bin/npgs/html.

Frijol azu frado; Mexico; bean USDA# PI510638; Aug. 9, 1994; http://www.ars–grin.gov/cgi–bin/npgs/html.

Frijo. Mayocoba; Mexico; bean USDA# PI510640; Aug. 9, 1994; http://www.ars–grin.gov/cgi–bin/npgs/html.

Canario Chiquito; Mexico; bean USDA# PI510645; Aug. 9, 1994; http://www.ars–grin.gov/cgi–bin/npgs/html.

Canario; Mexico; bean USDA# PI533337; Aug. 9, 1994; http://www.ars–grin.gov/cgi–bin/npgs/html.

Canario; Mexico; bean USDA# PI533483; Aug. 9, 1994; http://www.ars–grin.gov/cgi–bin/npgs/html.

Canario; Mexico; bean USDA# PI533520; Aug. 9, 1994; http://www.ars–grin.gov/cgi–bin/npgs/html.

Canary; United States; USDA# PI549993; Aug. 9, 1994; http://www.ars–grin.gov/cgi–bin/npgs/html.

Secretaria De Agricultura Y Ganaderia; Solicitud de Inscripcion en el Registro Nacional de Varledades de Plantas; Mexico, D.F., 6 de Junio de 1978; 4 pages.

English Translation of Cite No.. 50.

Secretaria De Agricultura Y Recursos Hidraulicos; Solicitud de Inscripcion en el Registro Nacional de Varledades de Plantas; Los Mochis, SIN., Septiembre 25 de 1987, Genealogia II14FrMo–4–M–M; 4 pages.

English Translation of Cite No. 52.

Secretaria De Agricultura Y Recursos Hidraulicos; Solicitud de Inscripcion en el Registro Nacional de Varledades de Plantas; Los Mochis, SIN., Septiembre 25 de 1987, Genealogia II18FrMo–5–3–M; 4 pages.

English Translation of Cite No. 54.

Secretaria De Agricultura Y Recursos Hidraulicos; Solicitud de Inscripcion en el Registro Nacional de Varledades de Plantas; Mexico, D.F., 3 de Septiembre de 1992; 4 pages.

English Translation of Cite No. 56.

Secretaria De Agricultura Y Recursos Hidraulicos; Solicitud de Inscripcion en el Registro Nacional de Varledades de Plantas; Mexico, D.F., Septiembre 1˚de 1994, Genealogia II14FrMo–CB (2) CB (3) CB (4)–M–M; 4 pages.

English Translation of Cite No. 58.

Secretaria De Agricultura Y Recursos Hidraulicos; Solicitud de Inscripcion en el Registro Nacional de Varledades de Plantas; Mexico, D.F., Septiembre 1˚de 1994, ECCZT–10163–42CM (10)–M+M Canario Divex–8130× Roval Red; 4 pages.

English Translation of Cite No. 60.

Proctor to debut new bean, Montrose Dally Press, Friday, Nov. 10, 1995, pp. 5–6.

Draft Agreement with FAO to Place CGIAR Center In–Trust Collections of Plant Genetic Resources under the Auspices of FAO, Consultative Group on International Agricultural Research, May 1994.

Joint Statement of FAO and the CGIAR Centres on the Agreement Placing CGIAR Germplasm Collections Under the Ausprices to FAO; Consuttative Group on International Agricultural Research; Oct. 25, 1994; 2 pages.

CGIAR Center Statements on Genetic Resources, Intgellectual Property Rights and Biotechnology; Center Directors and Center Board Chairs of the Consultative Group on International Agricultural Research (CGIAR): May 1999; 40 pages.

Gepts, Paul; letter to Ms. J. Pletrinl; Oct. 21, 2002 with two attached experiments; 10 pages.

Johnson, William C, et al.; The Role of epistasis in controlling seed yield and other agronomic traits in an Andean× Mesoamerican cross of common bean (*Phaseolus vulgaris* L.); Euphytica 125: 69–79, 2002; © Kluwer Academic Publishers.

Voysest Voysest, Oswaldo; Mejoramiento Genético del Frijol (*Phaseolus vulgaris* L.); Legado de Varledades de Américan Latina 1930–1999; Publication CIAT No. 321; ISBN 958–694–032–2; Tlraje: 700 ejemplares; Impreso en Columbia; Septiembre del 2000.

Rohlf, F. James: NTSYSpc Numerical Taxonomy and Multivariate Analysis System, Version 2.00 User Guide; Deptartment or Ecology and Evolution; State University of New York; © 1997 by Applied Biostatistics Inc., ISBN: 0–925031–28–3; 31 pages.

Gepts, Paul; Development of an Integrated Linkage Map; Common Bean Improvement in the Twenty–First Century; Development in Plant Breeding; vol. 7; Chapter 3, © 1999 Kluwer Academic Publishers; pp. 53–91 and 389–401.

McClearn, P.E., et al.; Molecular and Phenotypic Mapping of Genes Controlling Seed Coat Pattern and Color in Common Bean (*Phaseolus vulgaris* L.); Brief Communication; The Journal of Heredity 2002:93(2); pp. 148–152.

Gepts, Paul; Origin and Evolution of Common Bean: Past Events and Recent Trends; Colloquium; HortScience. vol. 33(7) Dec. 1998; pp. 1124–1130.

Gepts, P., et al.; Genetic Diversity in Pearl Millet (*Pennisetum glacum* [L.] R. Br.) at the DNA Sequence Level; The Journal of Heredity 1989:80(3): pp. 203–208.

Singh, Shree, P., et al.; Races of Common Bean, *Phaseolus vulgaris* L.; Current topics in breeding of common bean; S. Beebe (ed.), Working Document No. 47, 438 pp. Bean Program, CIAT, Cali, Colombia, p. 75–89, 1989.

Vos, Pieter, et al., AFLP: a new technique for DNA fingerprinting; © 1995 Oxford University Press; Nucleic Acids Research, 1995, vol. 23, No. 21 4407–4414.

Prakken, R.; Inheritance of Colours in *Phaseolus vulgaris* L. III on Genes for Red Seedcoat Colour and a General Synthesis; Mededelingen Landbouwhogeschool Wageningen—Nederland—72–29 (1972); Department of Genetics, Agricultural University, Wageningen, The Netherlands.

Prakken, R.; Inheritance of Colour in *Phaseolus vulgaris* L. II A Critical Review; Mededlingen Landbouwhogeschool, Wageningen, Nederland 70–23 (1970); Department of Genetics, Agricultural University, Wageningen, The Netherlands.

Efron, B.; The 1977 Rietz Lecture; Bootstrap Methods: Another Look at the Jackknife; Stanford University; The Annals of Statistics 1979, vol. 7, No. 1, 1–26.

Annual Report of the Bean Improvmeent Cooperative; vol. 28; 1985; pp. 87–88.

$1^{st}$ Annual Report [also $2^{nd}$ A.R.] of the Bean Improvement Cooperative; 1959; pp. 2 and 23.

Bassett, Mark J.; The Dark Corona Character in Seedcoats of Common Bean Cosegregates with the Pink Flower Allele$^{lae}$; J. Amewr. Soc. Hort. Sci. 120(3):520–522. 1995.

Bassett, Mark J.; A New Recessive Allele at the C Locus for Seedcoat Color in Common Bean; J. Amer. Soc. Hort. Sci. 120(6):896–899, 1995.

Gepts, Paul; The Use of Molecular and Biochemical Markers in Crop Evolution Studies; Evolutionary Biology, vol. 27; edited by Mark K. Hecht et al.; 1993 Plenum Press, New York; pp. 51–94.

Especies Y Varledades Recommendados Por La Sagar (Ciclos O.I. 97/98 Y P.V. 98/98) http://www.sagama.gob.mx/Pronase/productos/varxedo/sin.html.

Pronase (Indice de varledades de Frijol); http://www.sagama.gob.mx/Pronase/productos/ind_frijol.html; 1 page (Oct. 25, 20002).

Pronase (Varledades de Frijol); http://www.sagama.gob.mx/Pronase/productos/frijol.html; 15 pages (Oct. 25, 2002).

Defendants' Motion for Summary Adjudication that Plaintiff's Plant Variety Protection Certificate is Invalid, or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 4 pages.

Defendant's Brief In Support Motion for Summary Adjudication That Plaintiff's Plant Variety Protection Certificate is Invalid or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 52 pages.

Declaration of Victor Caro Ayala In Support Motion for Summary Adjudication That Plaintiff's Plant Variety Protection Certificate is Invalid, or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 18 pages.

Expert Report of Kenneth Grafton PH.D. In Support Motion for Summary Adjudication That Plaintiff's Plant Variety Protection Certificate is Invalid, or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 54 pages.

Expert Report of Paul Gepts PH.D. In Support Motion for Summary Adjudication That Plaintiff's Plant Variety Protection Certificate is Invalid, or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 55 pages.

Declaration of Robert J. Brunner In Support Motion for Summary Adjudication That Plaintiff's Plant Variety Protection Certificate is Invalid, or in the Alternative not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 11 pages.

Declaration of Octavio Garcia In Support of Motion for Summary Adjudication That Plaintiff's Plant Variety Protection Certificate is Invalid, or in the Alternative is not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 43 pages.

Expert Report of Llc. Marcial Garcia In Support Motion for Summary Adjudication That Plaintiff's Plant Variety Protection Certificate is Invalid, or in the Alternative not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 208 pages.

Declaration of Edward M. Jordan In Support of Motion for Summary Adjudication That Plaintiff's Plant Variety Protection Certificate is Invalid, or in the Alternative not Infringed; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 31, 2002; 308 pages.

Defendant Whitman Farms, Inc.'s Motion for Summary Judgment; filed in *Pod–Ners, LLC* v. *Northern Feed & Bean of Luceme. Ltd. Liability Co., et al.*, an action for Infringement of Pod–Ners' Plant Variety Protection Act Certificate currently pending in the United States District Court for the District of Colorado (Civil Action No. 01–WY–2310 AJ); Oct. 29, 2002; 5 pages.

Bukasov, S.M (1930) The Cultivated Plants of Mexico . . . Bull. Appl. Bot. Gen Pl. Breeding Leningrad Supp. 47 151–179.

Gepts, P. (1988) Phaseolin as an evolutionary morler. In Genetic resources of Plonecus beans. P Gepts (Ed) Kluwer Press p. 215–241.

Herrandez—Xolocotzi (1973) Plant introduction and germplasm of phaseolins. Seminar Series 2 E. CIAT, Colombia p. 253–258.

Herrandez et al. (1991) Contributions to knowledge of beans in Mexico. Ed. M. Engleman. Charingo p. 113–138.

Kaplan L. (1980) Variation in cultivated beans. In Coreltoro Cave. Ed T.F Lynch Academic Press 145–148.

Kaplan, L & Lynch T F (1999) Phaseolin in Ardeology Economic Botany 53(2) 261–272.

Voyest O. and Dessert M. (1991) Introduction as General descriptive Termology for Beans In Common Beans CABI p. 119.

Voyest, O. (1983) Varieties of Beans in Latin America. CIAT, Coli p. 87.

Masaya, P. & White J. W (1991) In Common Beans CABI. p. 445–499.

White, J.W (1991) Physiology of Yeild and pilenticil stress Physiology. In. Common Beans CABI p. 287–382.

Webster et al (1977) A monplodiozal study of the. J. Amer Soc. Hort–Sci 10(2) 640–643.

Gepts P. (1988) Phaseolin as an evolutionary Mater. In Genetic Resources of Phaseolin Beans. Kluwer Press p. 213–241.

Voyest, O (1983) Varieties of Bean in Latin America CIAT. (see color photos).

Salinas Perez & Ildes(anse R. I 1983) Breeding & Varieties Sarh, Mexico p. 45–67 (52–64 translated).

CIAT. Germplasm Catalog (1992) CIAT. Colombia p. 124–plus lables.

USDA, Holand, Plant Introduction Inventory (1968) p. 59–66.

Heneondez E. (1973) Plant Introduction and Cemmlanion CIAT Senon Series 2E. CIAT Colombia 253–258.

Bliss, F A. (1980) Common Bean. From American Society of Agonsmy & Crop Science, Madison, Wisconsin 273–284.

Annual Report of Bean Improvement Cooperative. (1996) vol. 39 1–19.

Leakey C L A (1988) Cenitypiee Plenitypic Markers in Common Bean. Klewer 245–327.

Annual Report of Bean Improvement Cooperative. (1982) vol. 25 109–127.

Yarnell, S.H. (1965) Cytogeneties of Vegetable Crops BST Rev. 31 247–327.

Buishand T. J. Crossing of Beans. (1956) Euplylica 5 41–50.

\* cited by examiner

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1-15 are cancelled.

\* \* \* \* \*